(12) United States Patent
Madole

(10) Patent No.: US 6,719,640 B1
(45) Date of Patent: Apr. 13, 2004

(54) POSTURE TRAINING DEVICE AND METHODS FOR USING SAME

(75) Inventor: Darrin E. Madole, Irvine, CA (US)

(73) Assignee: Balanced Health, Inc., Santa Ana, CA (US)

( * ) Notice: Subject to any disclaimer, the term of this patent is extended or adjusted under 35 U.S.C. 154(b) by 0 days.

(21) Appl. No.: 09/595,450

(22) Filed: Jun. 16, 2000

(51) Int. Cl.$^7$ .............................................. A63B 69/36
(52) U.S. Cl. ........................................ 473/215; 602/19
(58) Field of Search ................................ 602/17–19, 5, 602/32, 36; 2/44, 46, 467, 468; 128/869–870; 473/207–208, 266, 274, 277, 215, 458, 464; 482/109–110, 51, 10; 434/252, 247

(56) References Cited

U.S. PATENT DOCUMENTS

| | | | | |
|---|---|---|---|---|
| 1,532,037 A | * | 3/1925 | Cahill | 2/463 |
| 1,916,789 A | * | 7/1933 | Fordham | 128/869 |
| 2,973,030 A | * | 2/1961 | Matthewson | 155/175 |
| 3,129,243 A | * | 11/1965 | Mack | |
| 3,346,257 A | * | 10/1967 | Whitney | 273/26 |
| 3,522,802 A | * | 8/1970 | Morton | 602/32 |
| 3,620,211 A | * | 11/1971 | Green et al. | 128/89 |
| 4,103,681 A | * | 8/1978 | Shanley | 602/32 |
| 4,139,132 A | * | 2/1979 | Fairchild, Jr. | |
| 4,143,654 A | * | 3/1979 | Sherman | 128/87 R |
| 4,361,259 A | * | 11/1982 | Chanter | 224/635 |
| 4,438,763 A | * | 3/1984 | Zablen | 128/133 |
| 4,475,543 A | * | 10/1984 | Brooks et al. | 602/19 |
| 4,580,555 A | * | 4/1986 | Coppess | 128/89 R |
| 5,101,815 A | * | 4/1992 | Langdon-Orr et al. | 602/12 |
| 5,199,940 A | | 4/1993 | Morris et al. | |
| 5,211,186 A | * | 5/1993 | Shoemaker et al. | 128/870 |
| 5,348,523 A | * | 9/1994 | Blount | 482/104 |
| 5,435,563 A | * | 7/1995 | Salvatore | 273/188 |
| 5,466,205 A | * | 11/1995 | McLane et al. | 482/140 |
| 5,542,674 A | | 8/1996 | Kim | |
| 5,868,691 A | | 2/1999 | Vishnevsky | |
| 5,913,405 A | * | 6/1999 | Bordier | 2/467 |

FOREIGN PATENT DOCUMENTS

| | | | | |
|---|---|---|---|---|
| EP | 0134727 A1 | * | 3/1985 | A41D/13/00 |
| GB | 2225708 A | * | 6/1990 | A41D/13/00 |

* cited by examiner

Primary Examiner—Nicholas D. Lucchesi
Assistant Examiner—Huong Q. Pham
(74) Attorney, Agent, or Firm—Stout, Uxa, Buyan & Mullins, LLP; Donald E. Stout

(57) ABSTRACT

A device for improving the posture of a user when the user is engaged in certain activities, such as swinging a golf club, comprises an elongated rigid member having a securement element or strap extending therefrom. The rigid member has a length extending along the back of the user and the strap is adapted to secure the elongated rigid member to the user. The length of the rigid member is sufficient that a lower end of the rigid member is disposed at or below the waist of the user and an upper end of the rigid member is disposed behind the head of the user. Importantly, the head of the user is unattached to the rigid member, so that the user's body is free to flex and rotate in the performance of the certain activity. The device is designed to provide tactile stimulation to help improve motor learning responses, thereby increasing the possibility for behavior modification with respect to the assumption of appropriate postures during the desired activity.

9 Claims, 2 Drawing Sheets

POSTURE TRAINING DEVICE AND METHODS FOR USING SAME

BACKGROUND OF THE INVENTION

This invention relates generally to posture training devices, and more particularly to devices and methods for training a user to improve motor learning responses, thereby increasing the possibility for behavior modification with respect to appropriate postures while performing certain activities, including, in particular, swinging a golf club.

A common characteristic of many different types of otherwise unrelated activities is the necessity of good posture in order to perform them successfully and without undue risk of injury. In particular, appropriate spinal posture (in layman's terms, a "straight spine") is critical to ensuring a good result and preventing back injury. One activity of particular interest is the act of swinging a golf club. One of the most difficult activities to master in the sports world, a good and consistent golf swing requires the maintenance of appropriate spinal posture, with the golfer's spine lying along a plane which is roughly orthogonal to the plane along which the golf club lies. Additionally, it is important that the golfer avoid what is commonly referred to as a "head-up" orientation. Rather, the golfer's head should be in a "chin retracted" orientation, roughly aligned with the golfer's spine, but capable of flexure and rotation as required during the activity.

A typical approach for training a golfer to maintain proper posture during the act of swinging a golf club is for a trainer to employ a golf club as a standard, by laying it along the spine of the trainee, so that the trainee feels the club and maintains his spine in alignment therewith. The club shaft is held upwardly behind the trainee's head as well. The golfer is to keep his or her head in a "chin retracted" orientation, with the back of the head in contact with the club. The club thus provides "tactile feedback" that the golfer is maintaining appropriate posture. Of course, while this is an effective simulated training technique, because someone is required to hold the club shaft in position along the trainee's back, two people are required. There is no opportunity for the golfer to reinforce his or her lesson by practicing at home. It is also awkward and tiring to maintain the golf club shaft in such a position manually for any length of time.

As is disclosed in U.S. Pat. No. 5,868,691 to Vishnevsky, posture training devices are known which comprise a rigid member which is securable to the back of a person. The rigid member extends along the spine of the person to help the person maintain good posture, with the back in a relatively straight position. However, this type of device is not suitable for training a golfer to properly swing a golf club, for example. As shown in FIG. 2 of the '691 patent, the device is inappropriate for assisting the golfer in maintaining an "active chin retracted" orientation of the head during the act of swinging. Worse yet, the '691 patent teaches that the rigid member should be attached to the head of the person who is wearing the device. Holding the person's head in a specific posture limits rotation of the spine, and does not give the golfer the capability to flex and rotate the head in response to the demands of the act of the swinging the golf club.

Thus, what is needed is a posture training device and associated method which is specifically designed for certain activities which require appropriate spinal posture. The device should also be simple to use and inexpensive to manufacture, as well as being convenient to put on and remove, and should be attachable to the user in such a manner that it remains securely in place during vigorous activity.

SUMMARY OF THE INVENTION

The present invention solves the foregoing problems by providing such a device. The inventive device is particularly designed to provide tactile stimulation to help improve the motor learning responses of the user when engaged in certain activities, such as the swinging of a golf club, thereby increasing the possibility for behavior modification in regard to appropriate postures to be assumed during those activities.

More particularly, a device for improving the posture of a user when the user is engaged in certain activities is provided which comprises an elongated rigid member having at least one securement element extending therefrom. The rigid member has a length extending along the back of the user and the at least one securement element, which preferably comprises a strap, is adapted to secure the elongated rigid member to the user. Importantly, the length of the rigid member is sufficient that a lower end of the rigid member is disposed at or below the waist of the user and an upper end of the rigid member is disposed substantially behind the head of the user. However, an important aspect of the invention is that the head of the user must be unattached to the rigid member, and therefore free to flex and rotate with respect thereto. In other words, "active" contact of the head of the user on the device is desired, without limiting spinal rotation at any segmental level. The person cannot be held in a specific posture by the device, but rather the device should provide immediate tactile feedback that the person is actively holding the correct, or appropriate, posture. This "appropriate posture" will vary, depending upon the activity which is being pursued.

The person's head is to maintain contact with the rigid member of the device, through "active chin retraction", but, because the head is not strapped to the rigid member, the person is free to flex and rotate as required to properly pursue the activity.

In another aspect of the invention, there is provided a device for improving the posture of a user when the user is engaged in certain activities. The inventive device comprises an elongated rigid member having at least one strap extending therefrom, wherein the rigid member has a length extending along the back of the user and the at least one strap is wrapped around and secured to a portion of the body of the user. The rigid member has lower and upper ends, wherein the lower end is disposed at or below the waist of the user and the upper end is disposed behind the head of the user, wherein the rigid member is not attached to the user's head, thereby permitting the user to be free to flex and rotate with respect to the rigid member.

In still another aspect of the invention, there is disclosed a method for improving the posture of a user when the user is engaged in a certain activity. The disclosed method comprises a step of disposing an elongated rigid member along the back of the user. The elongated rigid member has at least one securement element extending therefrom, wherein a lower end of the elongated rigid member is disposed at or below the waist of the user and an upper end of the elongated rigid member is disposed behind the head of the user. In a second step, the elongated rigid member is attached to the body of the user using said at least one securement element. Then, the user's body is positioned in an orientation suitable for engaging in the certain activity, with the user's head being oriented to avoid being held to the upper end of the elongated rigid member. Preferably, when the method is being practiced in conjunction with the activity of swinging a golf club, the positioning step includes holding the head of the golfer in an "active chin retracted" orientation, wherein the golfer's body is free to flex and rotate, but maintains contact with the elongated rigid member.

The invention, together with additional features and advantages thereof, may best be understood by reference to the following description taken in conjunction with the accompanying illustrative drawing.

DESCRIPTION OF THE PREFERRED EMBODIMENT

Figure 2:
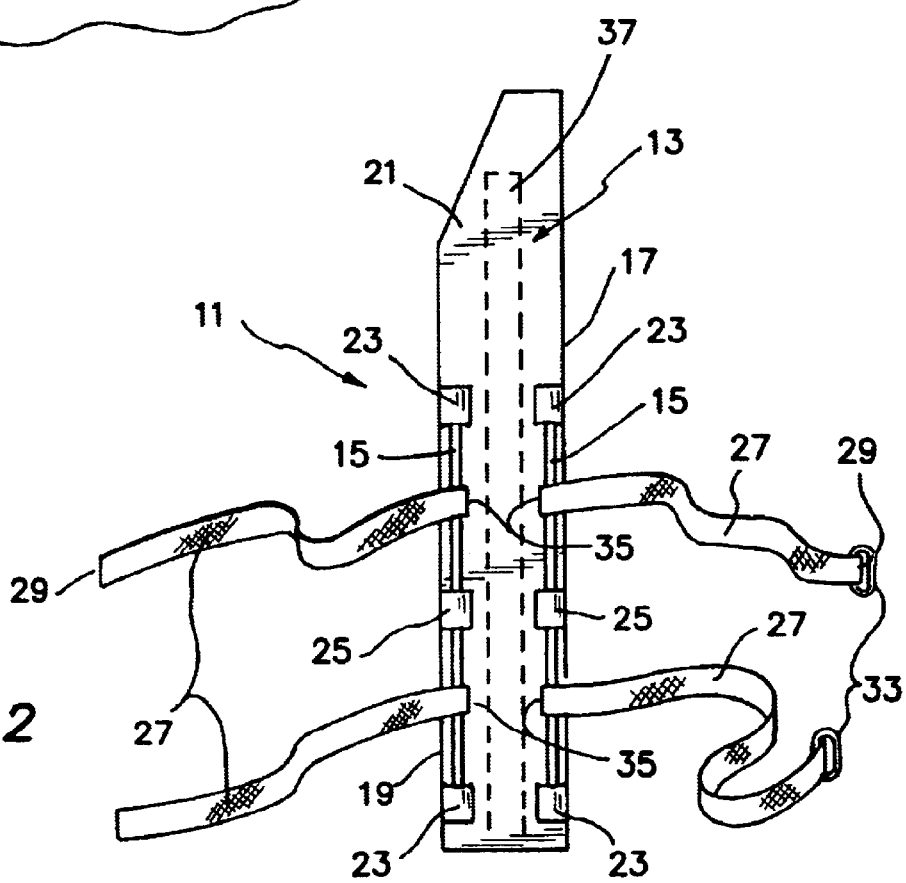
FIG. 2 is an elevational view of a first preferred embodiment of the present invention.

Referring now more particularly to the drawings, there is shown in FIG. 2 a first embodiment of the inventive posture training device 11, which device comprises an elongated rigid member 13. The elongated rigid member 13 includes a pair of rigid shafts or rods 15, preferably made of metal such as steel, which extend along opposing edges 17 and 19, respectively, of the member 13. A fabric cover 21 is disposed about the shafts 15. The shafts 15 are secured within the fabric cover 21 by means of end pockets 23, which are preferably sewn into the cover 21. The respective ends of each of the shafts 15 are disposed in one of the end pockets 23, as shown in FIG. 2. Intermediate fabric loops 25 are preferably disposed on the fabric cover 21, at a location which is approximately one-half of the distance between two opposing end pockets 23, for assisting in the retention of the shafts 15 in the fabric cover 21. The loops 25 are also preferably sewn onto the cover 21, and the shafts 15, when properly installed in the cover 21, are slid beneath the loops 25, as shown.

Figure 1:
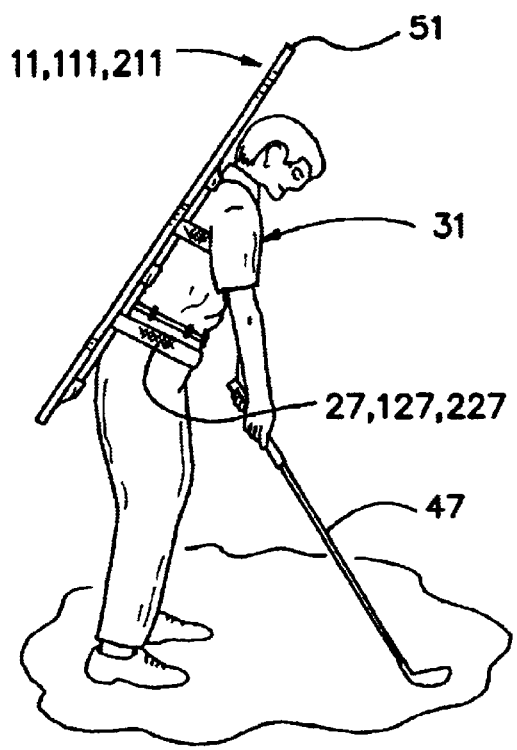
FIG. 1 is an elevational view of a golfer wearing the inventive golf/lift posture training aid during a practice golf session.

Attached to each of the shafts 15 are a plurality of securement elements 27, which preferably comprise straps. Each strap 27 comprises a free end 29, and the straps are adapted to extend about the torso of a user 31, as shown in FIG. 1, such that the two free ends 29 of corresponding straps 27 are connected to one another, thereby securing the member 13 to the user 31. A clasp mechanism 33, such as a buckle, hook and loop fasteners (commercially available under the trademark VELCRO), or other equivalent known fastening means, is disposed on one of the corresponding strap free ends 29, or complementary portions of the clasp mechanism 33 are disposed on each of the corresponding strap free ends 29, depending upon the nature of the clasp mechanism. For example, if the clasp mechanism is a hook and loop fastening system, then the hooks would be disposed on one free end, and the loops on the other.

The attachment end 35 of each of the securement straps 27 is preferably slidably attached to one of the shafts 15, as illustrated in FIG. 2. This slidable attachment in the preferred embodiment is a direct strap/shaft attachment. Specifically, the attachment end of the strap 27 is formed into a loop about the shaft 15 and sewn in place, with a sufficient clearance between the interior surface of the loop and the shaft to permit sliding of the strap between one of the end pockets 23 and the intermediate loop 25. Alternatively, a slider mechanism of a known type could be installed on the shaft 15, with the strap being secured to the slider mechanism. Whichever means for sliding is employed, the purpose is to permit the user to adjust the height of each strap relative to the length of the member 13 so that an appropriate fit is achieved.

To maintain proper rigidity of the elongated rigid member 13, a rigid element 37 is preferably disposed within the fabric cover 21, between the two shafts 15 and extending at least most of the length of the member 13. The rigid element 37 is shown in phantom, because it is preferably sewn into the cover 21, and is therefore invisible to those viewing the device 11. This element 37 is preferably flat stock, formed of hard plastic or similar material. The fabric cover 21 is preferably a padded foam, of the type typically used for orthopedic wrist braces, for example, which is covered with a suitable fabric material, such as canvas. This material results in significant comfort for the user.

Figure 3:
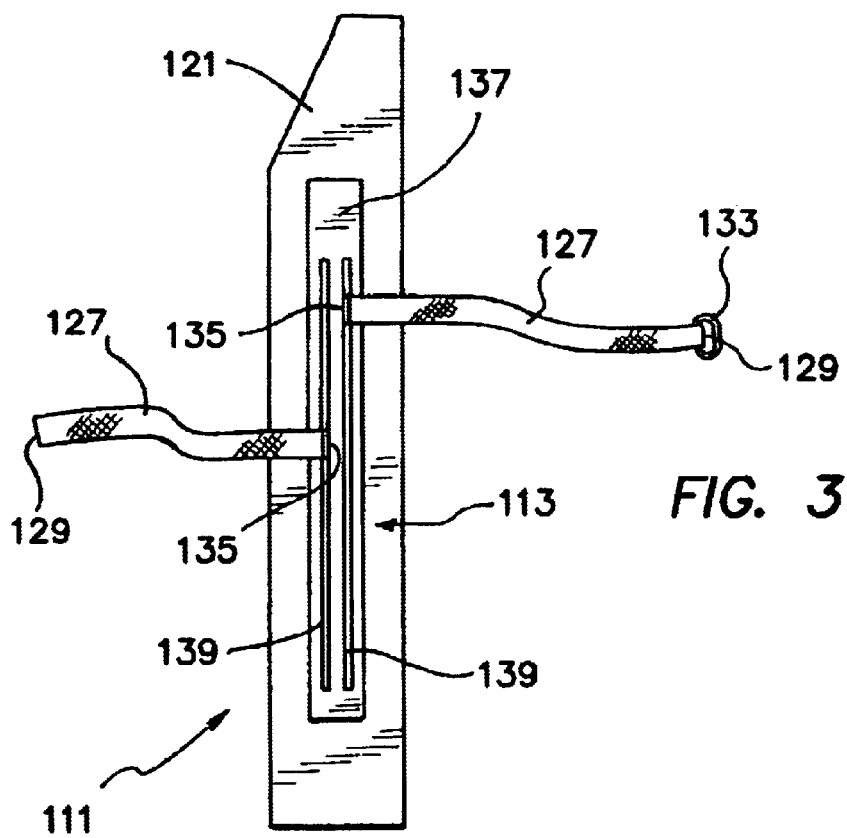
FIG. 3 is an elevational view similar to FIG. 2 of a second embodiment of the present invention.

Now with reference to FIG. 3, a modified embodiment of the inventive posture training device 111 is illustrated, wherein like elements to those in the FIG. 2 embodiment are designated by like reference numerals, preceded by the numeral "1". In this embodiment, the elongated rigid member 113 is constructed in a similar manner as the elongated rigid member 13 in the FIG. 2 embodiment, except that, instead of employing a pair of rigid rods or shafts 15 for securing the member 13 to securement elements or straps 27, the rigid member 113 utilizes a single center rigid element 137, similar to rigid element 37 of the FIG. 2 embodiment, which is preferably formed of flat stock such as metal or hard plastic. The difference between rigid elements 37 and 137 is that the rigid element 137 is exposed to the exterior of the fabric cover 121, so that the straps 127 can be attached thereto. Also, slots 139 are disposed in the rigid element 137, which are adapted to receive the attachment ends 135 of each of the straps 127, in such a manner that they are slidable therealong, in order that the straps 127 may be adjusted lengthwise to fit a user. Preferably, a trolley (not shown) is utilized to slide along each slot 139, and the attachment ends 135 of the straps 127 are secured to respective ones of the trolleys. Other equivalent methods for slidably securing the attachment ends of the straps to the rigid element 137 could be used as well, of course. Additionally, though two straps are shown in the FIG. 3 embodiment, and four straps are shown in the FIG. 2 embodiment, any number of straps may be used in any of the embodiments illustrated in the present application, as long as there are a sufficient number to ensure a good fit of the device 11, 111 to the user 31.

Figure 4:
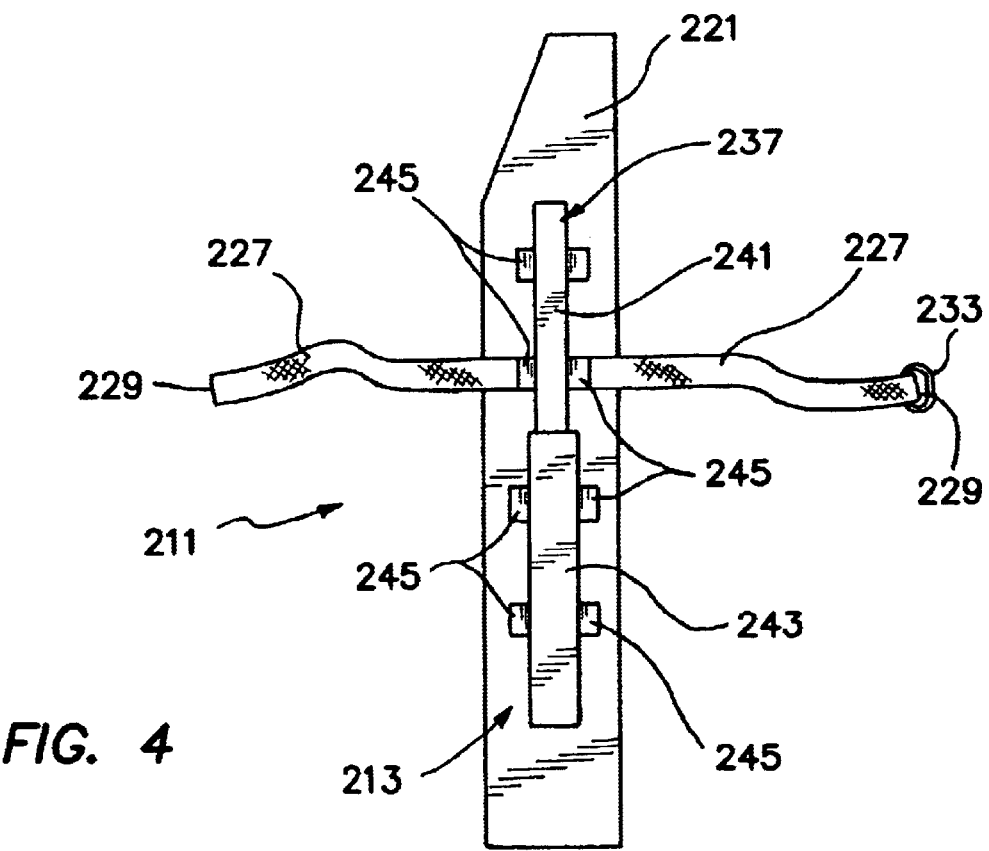
FIG. 4 is an elevational view similar to FIGS. 2 and 3 of a third embodiment of the present invention.

Still another modified embodiment of the inventive training device 211 is illustrated in FIG. 4, wherein like elements as are illustrated in the FIGS. 2 and 3 embodiments are designated by like reference numerals, preceded by the numeral "2". In this embodiment, the elongated rigid member 213 is constructed in a similar manner as the elongated rigid member 113 in the FIG. 3 embodiment. The difference between rigid elements 137 and 237 is that the rigid element 237 comprises a telescoping shaft, formed of a first telescoping member 241 and a second telescoping member 243, wherein the member 241 telescopes into the member 243, to form a shaft of a desired length for optimizing the fit of the device 211 to a particular user. It should be noted that this telescoping feature is usable in any of the illustrated embodiments, for any of the rigid elements 37, 137, 237 or for the shafts 15, if desired. Another difference between the elements 137 and 237 is that the element 237 has secured thereon a plurality of spaced coupling rings 245, to any of which the attachment ends of the straps may be attached. Thus, rather than slidably adjusting the position of each strap 227 relative to the length of the member 213, in this embodiment the adjustment is made by moving the strap from one coupling ring 245 to another. This approach affords a cost advantage, as well as providing a simpler construction suitable for most applications. This approach, of course, could also be adapted for the embodiment of FIG. 2, if desired.

Now with reference to FIG. 1, a preferred method for using the posture training device 11, 111, 211 will be described. One of the preferred usages for the device 11, 111, 211 is for the purpose of training a golfer to employ a correct golf swing. This entails orienting the body so that the trunk is flexed and the spine is straight (in other words, the user should assume appropriate spinal posture). The orientation of the spine of the user 31 should be approximately orthogonal to that of a golf club 47 which he or she is gripping. Additionally, it is important when swinging a golf club to assume an "active chin retracted" orientation, wherein the chin is retracted relative to the remainder of the face (resulting in a slight "head down" orientation), but the back of the head is in alignment with the spine, as shown in FIG. 1.

Thus, in accordance with the inventive method, the elongated rigid member 13, 113, 213 is secured onto the body of the user 31, as illustrated in FIG. 1, by disposing it along the user's back, so that a lower end 49 of the elongated rigid member 13, 113, 213 is disposed at or below the waist of the user 31, and an upper end 51 being disposed behind and preferably substantially above the head of the user 31. The upper end 51 of the rigid member 13, 113, 213 should not be attached to the head of the user, because it is important that the user's head be able to move freely (flex and rotate) relative to the rigid member.

In practice, as the user 31 swings the golf club 47, the elongated rigid member functions to ensure that the user's spine remains straight, in appropriate spinal posture. Additionally, the elongated rigid member, and particularly the upper end 51 thereof, functions to keep the user's head in a "chin retracted" orientation. In particular, this occurs because the rigid member, located behind the head, provides immediate tactile feedback that the person is actively holding this correct posture, because the back of the head of the person will be in contact with the rigid member. Should the person slump into an incorrect posture, the head will no longer be in contact with the rigid member, and this loss of contact should provoke a correction on the part of the golfer to appropriate spinal posture.

The inventive device can be used, as well, for other applications which require a flexed trunk and appropriate spinal posture. For example, the device is useful for providing assistance in training a user to maintain appropriate spinal posture when a user is engaged in lifting exercises, such as squats, so that the lifting is done by the legs and not by the back, for the purpose of avoiding a back injury. The inventive device can also be used to train users to perform numerous other activities which require appropriate spinal posture.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A device for improving the posture of the body of a user when the user is engaged in certain activities, comprising:

an elongated rigid member having a surface adapted for engagement with the user's body, said rigid member having a length sized and configured to extend along the back of the user, from a lower end disposed at or below the waist of the user to an upper end disposed behind the head of the user, above the user's neck, said elongated rigid member further comprising a rigid element which extends along more than half of the length of said rigid member, and a fabric cover disposed about said rigid element, and additionally comprising at least one rigid shaft; and at least two securement elements extending from said elongated rigid member and disposable about the torso of the user to secure the elongated rigid member to the body of the user, wherein no portion of any securement elements are disposed over the shoulders of said user when the elongated rigid member is secured to the body of the user;

said elongated rigid member surface being substantially planar along its entire length, in that there are no pads or cushions disposed anywhere on said surface which protrude outwardly from said surface;

wherein said elongated rigid member is not attachable to a head of the user when the elongated rigid member is secured to the body of the user.

2. The device as recited in claim 1, wherein said at least two securement elements comprise straps.

3. The device as recited in claim 1, wherein said securement elements are attached to said rigid element.

4. The device as recited in claim 1, wherein said securement elements are attached to said at least one rigid shaft.

5. The device as recited in claim 1, wherein a location of at least one of said at least two securement elements is adjustable relative to the length of said elongated rigid member.

6. A device for improving the posture of the body of a user when the user is engaged in certain activities, comprising:

an elongated rigid member having a surface adapted for engagement with the user's body, said rigid member having a length sized and configured to extend along the back of the user, from a lower end disposed at or below the waist of the user to an upper end disposed behind the head of the user, above the user's neck, said elongated rigid member further comprising a rigid element, and a fabric cover disposed about said rigid element, wherein said rigid element comprises two telescoping members, so that the length of said elongated rigid member is adjustable; and at least two securement elements extending from said elongated rigid member and disposable about the torso of the user to secure the elongated rigid member to the body of the user, wherein no portion of any securement elements are disposed over the shoulders of said user when the elongated rigid member is secured to the body of the user;

said elongated rigid member surface being substantially planar along its entire length, in that there are no pads or cushions disposed anywhere on said surface which protrude outwardly from said surface;

wherein said elongated rigid member is not attachable to a head of the user when the elongated rigid member is secured to the body of the user.

7. The device as recited in claim 1, where the elongated rigid member is sized and configured to extend substantially above the user's head when attached to the user.

8. A method for improving the posture of a user's body when the user is engaged in swinging a golf club, comprising:

disposing an elongated rigid member along the back of the user, wherein a lower end of the elongated rigid member is disposed at or below the waist of the user and an upper end of the elongated rigid member is disposed behind the head of the user, above the user's neck;

securing the elongated rigid member to the user's body by fastening a securement element attached to the elongated rigid member about the torso of the user; and maintaining substantial alignment of the user's head with a lower portion of the user's spine, said lower spine portion being the spine portion below the user's neck, by maintaining contact between the back of the user's head, above the neck, and the upper end of the elongated rigid member while the user is standing in an upright orientation and while swinging a golf club, without attaching the user's head directly to the elongated rigid member.

9. The method as recited in claim 8, wherein the step of maintaining contact between the back of the user's head, above the neck, and the upper end of the elongated rigid member is performed by retracting the chin of the user relative to the rest of the user's face, so that the user's head is in a slight "head down" orientation during the performance of the certain activity.

* * * * *